United States Patent [19]

Gewartowski

[11] 4,190,520
[45] Feb. 26, 1980

[54] HYDROCARBON CONVERSION PROCESS

[75] Inventor: Steve A. Gewartowski, Mt. Prospect, Ill.

[73] Assignee: UOP Inc., Des Plaines, Ill.

[21] Appl. No.: 866,663

[22] Filed: Jan. 3, 1978

[51] Int. Cl.² ............................................. C10G 35/04
[52] U.S. Cl. ........................................ 208/95; 208/46; 208/100
[58] Field of Search ............... 208/46, 365, 370, 95, 208/103, 100; 196/134

[56] References Cited

U.S. PATENT DOCUMENTS

| | | | |
|---|---|---|---|
| 1,729,215 | 9/1929 | Hanna | 208/365 |
| 2,284,493 | 5/1942 | Noll et al. | 196/134 |
| 2,666,022 | 1/1954 | Johnson | 208/46 |
| 2,711,385 | 6/1955 | Hannah | 196/134 |
| 3,725,249 | 4/1973 | Vesely et al. | 208/139 |

*Primary Examiner*—Herbert Levine
*Attorney, Agent, or Firm*—James R. Hoatson, Jr.; John F. Spears, Jr.; William H. Page II

[57] ABSTRACT

Problems associated with heating the mixed-phase feed stream of a hydrocarbon conversion process are reduced by a method of operation which includes heating the feed stream to a sufficient temperature for passage into a reaction zone by indirect heat exchange. The effluent stream of the reaction zone is then further heated in a fired heater and is passed through the indirect heat exchange zone in which the feed stream was heated.

13 Claims, 1 Drawing Figure

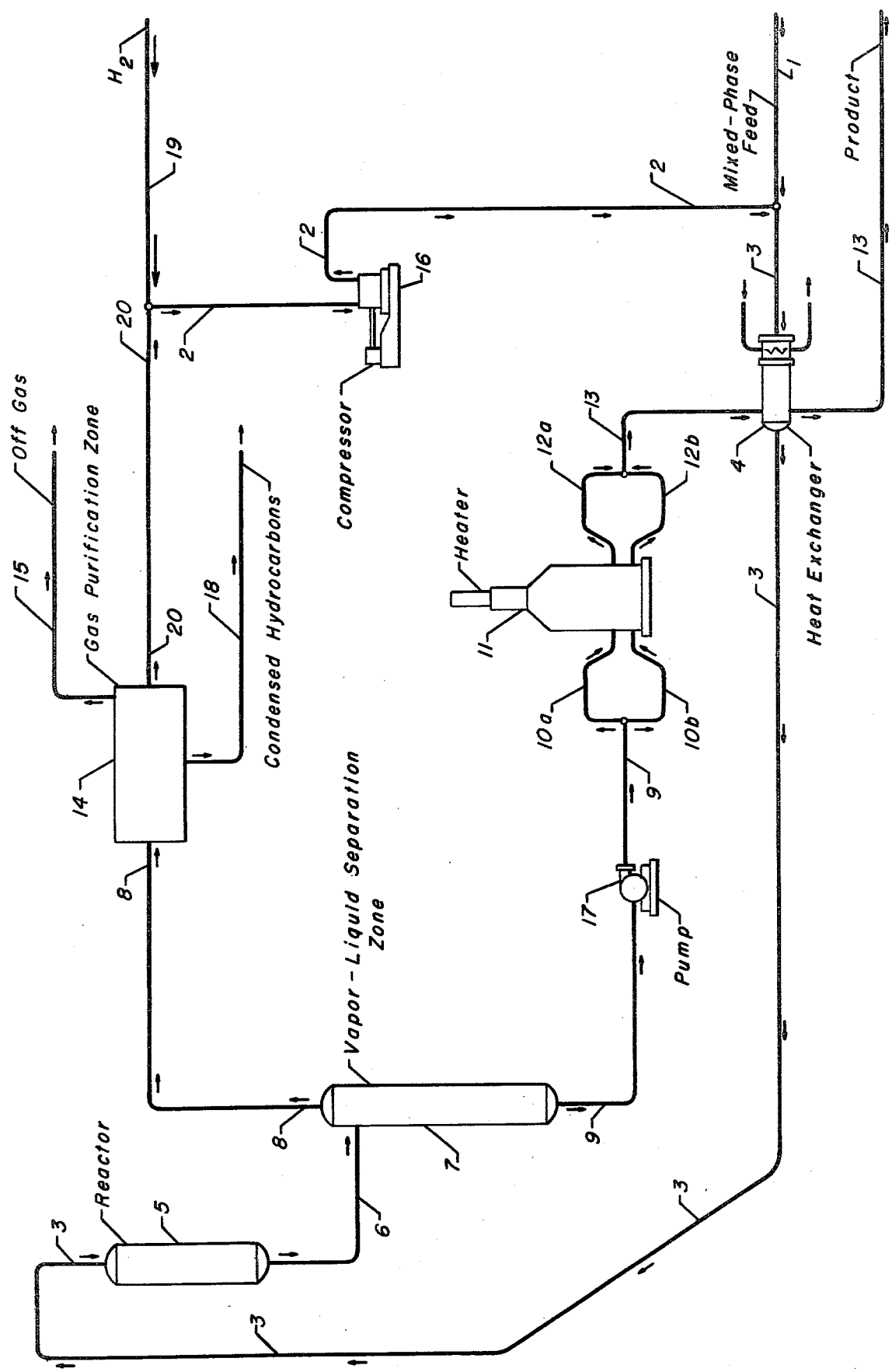

HYDROCARBON CONVERSION PROCESS

FIELD OF THE INVENTION

The invention relates to a process for the treating or refining of mineral oils and other hydrocarbonaceous fluids. The invention more specifically relates to a hydrocarbon conversion process wherein a mixed-phase feed stream is passed through a reaction zone at a high temperature. The invention also relates to the use of indirect heat exchange to recover heat from the effluent stream of a reaction zone. The invention may be applied to many processes described in the references found in Classes 260 and 208. These processes include hydrodesulfurization, hydrocracking and isomerization.

PRIOR ART

The subject invention is one of general application and is not restricted to any specific type of reaction or reactant composition. It may therefore be applied to a great many processes which are well developed and are used commercially. Among these are the isomerization of paraffinic and aromatic hydrocarbons and the hydrotreating of black oils for the removal of sulfur and nitrogen.

Several steps are performed in the subject invention which are found in the prior art. For instance, it is well known to recover heat from an effluent stream of a reaction zone by the indirect heat exchange of the effluent stream against the feed stream charged to the reaction zone. It is also a well established practice to pass a mixed-phase reaction zone effluent stream into a phase separation zone to recover a vapor stream comprising hydrogen which is then recycled to the reaction zone as part of the feed stream. Another well established step in hydrocarbon conversion processes comprises supplying heat to a feed stream by passing the feed stream through a fired heating zone.

Heretofore, it has been a standard practice to heat the feed stream to a hydrocarbon conversion or separating unit by first heat exchanging it against a hot stream, such as the effluent of the unit, and then further heating it in a fired heater or other heating unit. The effluent stream of the unit may be passed into another processing unit or cooled.

BRIEF SUMMARY OF THE INVENTION

The invention provides a hydrocarbon conversion process which eases the processing of mixed-phase feed streams. The invention may also, in specific applications, lower the capital or utility cost of a hydrocarbon conversion process.

One broad embodiment of the invention may be characterized as comprising the steps of passing a mixed-phase feed stream into an indirect heat exchange zone and effecting the vaporization of the liquid phase portion of the feed stream and the heating of the feed stream to a desired temperature; passing the feed stream through a reaction zone maintained at hydrocarbon conversion conditions that effect the production of a reaction zone effluent stream having a higher enthalpy than the feed stream as the feed stream enters the reaction zone; heating the reaction zone effluent stream by passage through a fired heating zone; and cooling at least a portion of the reaction zone effluent stream by passage through the same indirect heat exchange zone and indirect heat exchange against the feed stream.

DESCRIPTION OF THE DRAWING

The Drawing illustrates one of the more limited embodiments of the invention as it may be applied to a hydrodesulfurization process. For simplicity and clarity, a number of pieces of apparatus normally required in the operation of the process have not been shown. This deleted apparatus includes pressure, flow and temperature control systems, vessel internals, etc., all which may be of customary design. This depiction of one embodiment of the invention is not intended to exclude from the inventive concept other embodiments set out herein or which are the result of normal and reasonable modification of those embodiments.

Referring now to the Drawing, a mixed-phase black oil feed stream comprising a mixture of sulfur-containing hydrocarbonaceous chemical compounds enters the process in line 1. The feed stream is then admixed with a hydrogen-containing gas stream from line 2 and passed through an indirect heat exchanger 4 via line 3. The feed stream is therein heated to the desired inlet temperature of the desulfurization reactor 5. This temperature increase will normally cause an additional amount of the feed stream to become vaporized. The mixed-phase feed stream is then contacted with catalyst at the hydrodesulfurization conditions maintained within the reactor, and hydrogen is consumed in the production of a reactor effluent stream which comprises hydrogen sulfide, hydrogen and liquid phase hydrocarbonaceous materials.

The reactor effluent stream is passed into a vapor-liquid separator 7 through line 6. The liquid phase components of the reactor effluent stream leave the bottom of the separator in line 9 as a liquid product stream. This stream is pressurized in the optional pump 17 and is then divided between lines 10a and 10b of the inlet manifold of the multi-pass fired heater 11. The liquid product stream is heated to a higher temperature than the reactor effluent stream in the heater and is removed from the heater in the outlet manifold lines 12a and 12b. It is then passed through the indirect heat exchanger 4 and cooled by heat exchange against the feed stream. The liquid product stream is then removed from the process in line 13.

The vapor phase portion of the reactor effluent stream is removed from the vapor-liquid separator in line 8 and passed into a gas purification zone 14. The purpose of this zone is to remove some of the ammonia, hydrogen sulfide and light hydrocarbons from the entering gases. This zone may utilize one or more partial condensations and an amine scrubbing operation. A resultant stream of condensate, which may comprise $C_5$ to $C_8$ hydrocarbons, is removed in line 18, and hydrogen sulfide and light gases such as methane and ethane are vented through line 15. The remaining relatively hydrogen-rich recycle gas stream is removed in line 20 and admixed with the makeup hydrogen stream carried by line 19. The resultant hydrogen-containing gas stream is pressurized in the recycle compressor 16 and then admixed into the feed stream carried by line 1.

DETAILED DESCRIPTION

In a great many processes used in the petroleum, chemical and petrochemical industries, it is necessary to heat a process feed stream prior to passing the feed stream into a reaction zone. Often this feed stream is a mixed-phase stream having both vapor phase and liquid phase components. Another frequent occurrence is that the furnaces or heaters used to raise these feed streams to the proper inlet temperatures must be multi-pass heaters. The various problems associated with heating mixed-phase streams in multi-pass fired heaters therefore arise frequently.

One of the largest problems in heaters used in this particular service is the maldistribution of the vapor and liquid phases within the heater tubes. The result of this maldistribution may be very uneven temperature profiles between or within heater tubes and the creation of localized areas of excessive temperature. For instance, a large body of liquid which accumulates at a low point may block vapor flow through one or more tubes of the heater, thus disrupting the normal two phase flow and possibly resulting in periods of little or no flow in the tubes affected. The flow of these fluids through the heater tubes removes heat from the wall of the tubes and therefore serves to limit the maximum temperature reached by the tubes. Diminished or interrupted fluid flow decreases the rate of heat removal from the tubes by decreasing heat transfer to the fluids. This allows the tubes to reach higher temperatures which may cause coke deposits to form or may cause undesired thermocracking of the fluids. Long term maldistribution of the liquid flow may result in the tubes being weakened by excessive operating temperatures. This leads to the rupture of the heater tubes, and may cause the catastrophic leakage of the highly flammable feed stream into the heater.

It is therefore an objective of the invention to provide a hydrocarbon conversion process wherein the problems associated with the maldistribution of mixed-phase feed streams in fired heaters are reduced. It is another objective of the invention to improve the operation of processes utilizing multi-pass fired heaters. Further objectives of the invention are to provide processes for the hydroprocessing of black oils, and the isomerization of $C_4$ to $C_7$ paraffins and $C_7$ to $C_9$ aromatic hydrocarbons. As used herein, the term "hydroprocessing" is intended to include the more specific hydrocarbon conversion processes such as hydrotreating, hydrocracking and hydrodesulfurization. It therefore is considered generic to the saturation of olefins and diolefins contained in a pyrolysis gasoline, the hydrodesulfurization of a black oil and the removal of small amounts of nitrogen from feed streams by hydrodenitrification.

The subject invention utilizes both a heater, preferably a fired heater, and an indirect heat exchange means. Both of these pieces of apparatus may be designed and built using the customary standards and methods after adjustment to compensate for the changed conditions of temperature and pressure attributable to use of the invention. As used herein, the term "multi-pass heater" is intended to refer to a heater which has piping arranged to allow entering fluid to divide between several alternative flow paths through the actual high temperature heating area. The term "fired heater" is used to indicate an open flame is maintained within a heater. The invention is used in conjunction with a reactor or reaction zone. A fixed, moving, ebulliated or fluidized bed reaction zone may be used. The reaction zone may contain two or more reactors in series or parallel flow. The design and operation of the reaction zone may be the same as is customary for the specific conversion process being performed.

In the method of the invention, a mixed-phase feed stream is brought up to the desired inlet temperature of the reaction zone in an indirect heat exchange zone. Since the fluid quantities involved can be quite large, the surface area needed in the heat exchange zone may require the use of several banks of individual heat exchangers. The use of countercurrent flow in shell and tube exchangers is preferred, but other types of exchangers may be substituted. Besides being heated in the indirect heat exchange zone, a portion or all of the liquid material in the feed stream may be vaporized. In some conversion processes such as isomerization, vaporization of the total feed stream prior to the reaction step is normally required. In other processes, it is desired or necessary to utilize mixed-phase flow. One example of this is the low temperature hydroprocessing of pyrolysis liquids for the saturation of olefinic hydrocarbons. High temperatures are avoided in this process since they cause excessive polymerization of the olefinic hydrocarbons in the reaction zone.

One process in which mixed-phase reactants are used is the hydrocracking or hydrodesulfurization of black oils. As used herein, the term "black oil" is intended to indicate a petroleum fraction containing more than 1.0 wt.% asphaltenes and having a boiling point range, as determined by the appropriate ASTM distillation method, which extends above 650° F. Two of the more common refinery streams which are normally referred to as black oils are reduced crudes, that is the portion of a crude oil boiling above about 650° F. and containing from 1 to 15 wt.% asphaltenes, and vacuum column bottoms, which normally boil above about 975° F. and contain from about 1 to 20 wt.% asphaltenes. These very heavy materials cannot be vaporized at the required hydroprocessing conditions and therefore remain as a liquid phase.

After being heated in the indirect heat exchange zone, the feed stream is passed through the reaction zone. Various gas, recycle and additive streams can be admixed with the feed stream between the heat exchange zone and the reaction zone, but they are preferably added upstream of the heat exchange zone. A wide variety of reactions may be performed in the reaction zone. The specific reaction is preferably exothermic but may be endothermic. It is therefore preferred that the reaction zone effluent stream has a higher temperature and enthalpy than the reaction zone feed stream does as it enters the reaction zone. In some instances, such as hydrocracking, a much greater percentage of the reaction zone effluent may be in the vapor phase as compared to the feed stream entering the reaction zone.

At least a portion of the reaction zone effluent stream is passed into a heater. If the reaction zone effluent stream is totally vaporized, it is preferred that the entire effluent stream is passed into the heater and then heat exchanged against the feed stream. Two-phase flow through the heater is then totally avoided. If the reaction zone effluent stream is a mixed-phase stream, it is preferably passed into a vapor-liquid separation zone as shown in the Drawing. The vapor and the liquid phase portions of the reaction zone effluent stream are then separated into individual streams. Both or only one of these streams may be passed through the heating zone. If both streams are heated, they are at all times kept separate while in the heating zone. Preferably, only liquid phase is heated if it is present in a sufficient quantity. The heated portion of the reaction zone effluent stream is then passed through the indirect heat exchange zone to effect the heating of the feed stream.

In order to heat the feed stream to the desired inlet temperature of the reaction zone, it is necessary that the heated portion of the reaction zone effluent stream which is passed into the indirect heat exchange zone has a temperature above the desired inlet temperature of the reaction zone. The exact temperature required will depend on such factors as the flow rates of the two streams fed to the indirect heat exchange zone and the surface area available within this zone. The maximum possible amount of heated reaction zone effluent is equal to the flow rate of the feed stream, and a temperature difference or approach of at least 15 to 20 Fahrenheit degrees is normally required in an indirect heat exchanger. Therefore, the heated portion of the reaction zone effluent which is passed into the indirect heat exchange zone should, as a minimum, have a temperature 15 to 20 Fahrenheit degrees above the desired inlet temperature of the reaction zone.

The subject operating method has several advantages all which may not be present in any one particular application. For instance, in some processes, the reactor effluent may cause less fouling of the heater tubes than the feed stream even at a higher temperature utilized. Secondly, if the effluent of the reaction zone is a vapor phase stream, there is no possibility of liquid maldistribution in the heater. A third advantage is present when a mixed-phase reaction zone effluent stream is produced in a process having a recycle gas stream. In this situation, the pressure drop across the heater is out of the recycle gas circuit. This reduces the utilities cost of operating the process. An example of this type of process is the black oil hydrodesulfurization process presented in the Drawing.

Recycle gas streams are used in many processes including those for paraffinic and aromatic hydrocarbon isomerization. These recycle gas streams will often be rich in hydrogen and contain 80 to 90 mole percent or more hydrogen. Hydrogen may be passed through the reaction zone for several reasons. These include aiding the vaporization of the reactants, the maintenance of catalyst activity and the prevention of excessive coke deposition. In some processes, the desired purity of the recycle stream may be maintained rather easily, as by the use of a drag stream or by the judicious control of the amount of light material which is removed in various liquid streams including condensates. This is normally true of the typical isomerization processes. In hydrodesulfurization and hydrocracking processes, a large number of volatile materials, such as propane, methane and hydrogen sulfide are often formed. The light hydrocarbons can be removed by partial condensations and adsorption. The acidic hydrogen sulfide is often removed by contacting with an amine solution such as monoethanolamine. The operations performed in the gas purification zone of a desulfurization process may therefore include cooling the gas stream to a temperature of about 100° F. and countercurrently contacting the cooled gas stream with an aqueous amine solution in a contacting column. Further details on recycle gas purification in desulfurization processes may be obtained by reference to U.S. Pat. Nos. 3,725,252 and 3,847,799.

Catalysts suitable for use in many hydrocarbon conversion processes are available commercially from several sources. Many suitable hydroprocessing catalysts will comprise one or more metals listed in Group VIII or Group VI-B or compounds of these metals such as oxides or sulfides. The metallic components of Group VI-B are generally present in an amount within the range of about 4.0 to 30 wt.%. The Group VIII noble metals are preferably present in the range of about 0.2 to 10.0 wt.%. All concentrations of metals in catalyst are calculated on the basis of the elemental metal. The metallic components of the catalyst are supported on a porous carrier material. These carriers are typically one of the well known amorphous refractory inorganic oxides such as alumina, silica or a combination of the two. Zeolitic materials including mordenite, faujasite, and Type A or Type U molecular sieves may also be used as the carrier either separately or in combination with the amorphous carrier materials. The precise composition and specific method of manufacture of the catalysts used in this and other embodiments of the invention is not critical and may vary widely. A preferred hydroprocessing catalyst comprises sulfides or oxides of nickel, molybdenum and cobalt supported on a calcined carrier of alumina and silica.

The conditions maintained within the reaction zone are selected depending on such factors as the desired reactions, the composition of the feedstock and the activity of the catalyst. The operating conditions used during hydroprocessing will normally include a temperature between 500° F. and 1,000° F., and preferably from about 600° F. to 900° F. A broad range of operating pressures is from about 200 to 3,400 psig., with pressures below 2,500 psig. being preferred. Hydrogen will be circulated through the reaction zone at a rate of from about 200 to 25,000 SCF per barrel of charge, with circulation rates between 1,000 and 15,000 SCFB being preferred. The liquid hourly space velocity of the charge stock may vary widely from about 0.25 to 10.0. A preferred range for this is 0.5 to 3.0. Liquid or vapor quench streams may be passed into the reaction zone to limit the maximum temperature reached. Further details as to catalysts and process conditions for hydroprocessing may be obtained by reference to U.S. Pat. Nos. 3,725,252; 3,730,880; 3,748,261; 3,825,485; 3,847,799; 3,702,237; 3,364,131; 2,717,857 and 3,720,602. A rather detailed summary of the art of hydrocracking is provided by the article beginning at page 74 of *Industrial Engineering Chemistry, Product Research and Development*, Vol. 14, No. 2, 1975.

The operation of the heater, or more specifically the rate at which fuel is supplied to the heater, may be controlled by one or more temperature measurements taken at the inlet of the reaction zone or within the reaction zone. Temperature measurements used in the heater control system may also be taken as the feed stream exits the indirect heat exchange zone. The operation of the heater will be adjusted as required to provide the temperature required within the reaction zone for the desired degree of conversion. This temperature will vary as the catalyst ages. Other variables which may require adjustment of the rate of flow of fuel to the heater include the rate of flow of the feed stream and its initial temperature prior to entering the indirect heat exchange zone.

The effluent of the reaction zone is not cooled prior to passage into the vapor-liquid separation zone or into the heater. If a vapor-liquid separation zone is used, it may be designed and constructed in a customary manner. A great many designs for vapor-liquid separators exist. Representative examples are the apparatus shown in U.S. Pat. Nos. 3,364,657; 3,826,064; 3,853,513; 3,873,283 and 3,900,300. In many instances, a relatively simple knockout drum with a demisting blanket will be sufficient. Guidelines on the design of knockout drums are contained in the article at page 155 of the June, 1961 edition of *Hydrocarbon Processing and Petroleum Refiner*. Although the use of a vapor-liquid separation zone is preferred when the reaction zone effluent is a mixed-phase stream, the invention may be practiced in this instance without the use of a vapor-liquid separation zone. This could result from a desire to cool the effluent stream prior to separating it into liquid and vapor phases. Also, even if a vapor-liquid separation zone is not used, it may be advantageous to use the inventive concept when the reaction zone effluent stream contains less liquid phase material than the reaction zone feed stream.

In the preferred embodiment of the invention, a $C_7$ to $C_9$ aromatic hydrocarbon is isomerized in the reaction zone under vapor phase conditions as described in U.S. Pat. Nos. 2,784,241; 2,976,332; 3,078,318; 3,281,482; 3,304,339; 3,553,276 and 3,996,305. These references describe both catalysts and process conditions. An example of such a process is the isomerization of a mixture of xylene isomers in order to reestablish an equilibrium mixture of the isomers. This is performed commercially in combination with separatory processes which remove one or more of the isomers from a mixture of the isomers, with the remaining components of the equilibrium mixture being recycled to the isomerization process.

In the preferred embodiment, the reaction zone is operated at conditions effective to cause the isomerization of aromatic hydrocarbons. Besides the presence of a catalyst, these conditions include a temperature of about 0° C. to about 600° C., preferably 320° C. to about 450° C., and a pressure of from about 1.0 to 100 atmospheres. Preferred is a pressure in the range of about 7 to 28 atmospheres and the use of a single fixed bed reactor operated with a downward flow of vapor phase reactants. The rate of hydrogen circulation should be sufficient to maintain a hydrogen to hydrocarbon mole ratio of from 1:1 to 20:1 in the reactor. This ratio is preferably kept within the range of about 1.5:1 to about 5:1. The amount of catalyst loaded in the reactor should provide a weight hourly space velocity (weight of hydrocarbons passing through the reactor in one hour per unit weight of catalyst) of about 0.5 to about 10 and preferably about 1 to 5. The exact conditions employed will normally vary with the age of the catalyst and are set by the activity of the catalyst and the effect of the conditions on selectivity, conversion and ultimate yield of the isomerization zone.

Central to operation of the aromatic hydrocarbon isomerization zone is an effective isomerization catalyst. Several different suitable formulations are known to those skilled in the art and effective catalysts are available commercially. The catalyst will typically comprise an acidic inorganic oxide support such as alumina, silica-alumina mixtures, faujasites and mordenites which have been combined or impregnated with a metallic component. Preferred is an alumina based catalyst containing about 0.05 to about 5.0 wt.% of a Group VIII metallic component and 0.3 to 5.0 wt.% halogen. Particularly preferred is about 0.1 to about 1.5 wt.% of platinum or palladium and about 0.5 to 2.5 wt.% fluorine or about 0.1 to 1.5 wt.% chlorine. This halogen concentration may be maintained by the injection of halogen-containing substances such as carbontetrachloride into the material entering the isomerization zone. These catalytic composites may in addition contain from about 0.1 to about 1.0 wt.% sulfur to improve their performance. All percentages given in reference to catalyst composition are calculated on an elemental basis. Other catalysts which may be employed in the isomerization zone are described in some detail in U.S. Pat. Nos. 3,464,929; 3,409,685 and 3,409,686. The catalysts described in these references include an alumina matrix having less than 20 wt.% of finely divided mordenite dispersed in it and containing at least one metallic component chosen from nickel, platinum and palladium, about 0.001–2.0 wt.% sulfur and about 0.2 to 3.0 wt.% chlorine or fluorine. A second catalyst disclosed in these references has a base comprising an alumina matrix with less than 20 wt.% of finely divided mordenite dispersed in it and contains about 0.05 to 5.0 wt.% of platinum, or preferably palladium, and about 0.2 to 3.0 wt.% chlorine or fluorine. Other catalytic composites may also be used in the reaction zone.

The preferred embodiment of the invention may be characterized as a process for the isomerization of aromatic hydrocarbons which comprises the steps of passing a mixed-phase feed stream comprising a $C_7$ to $C_9$ aromatic hydrocarbon and hydrogen into an indirect heat exchange zone and effecting the vaporization of the liquid phase portion of the feed stream and the heating of the feed stream to a desired reaction zone inlet temperature; passing the feed stream through a catalytic aromatic hydrocarbon reaction zone maintained at aromatic hydrocarbon isomerization conditions that effect the production of a reaction zone effluent stream; heating the reaction zone effluent stream to a higher temperature by passage through a fired heating zone; and cooling all of the thus heated reaction zone effluent stream by passage through the indirect heat exchange zone and by the accompanying heat exchange against the feed stream.

In another embodiment of the invention, a normal paraffin having from four to seven carbon atoms per molecule is isomerized in the reaction zone. This process is described in U.S. Pat. Nos. 2,938,936; 3,112,351; 3,128,319; 3,131,235; 3,283,301 and 3,755,144. It is performed for several purposes including the upgrading of the paraffins to suitable motor fuel blending components or the production of isoparaffins for use in an alkylation process.

The preferred paraffin isomerization catalyst composition comprises an alumina-platinum composite, which has had chemically combined hydroxyl groups on its surface reacted with alumina chloride or another Friedel-Crafts type halide after the composite has been calcined. It may be exemplified by the catalysts disclosed by U.S. Pat. Nos. 2,999,074 and 3,649,704. The alumina-platinum composite may be prepared by any suitable method, such as coprecipitation or impregnation, and then mildly calcined at about 350° C. to 700° C., and preferably from 500° C. to 600° C. to remove adsorbed water but still retain hydroxyl groups on the catalyst surface prior to reaction with the halide. The isomerization catalyst may also comprise other metals such as germanium or rhenium in addition to the platinum.

In general, satisfactory paraffin isomerization catalysts comprise refractory inorganic oxides and a platinum group metal. The solid refractory oxide may be selected from silica, alumina, titanium dioxide, chromia, or mixtures of these oxides; various naturally occurring refractory oxides in differing degrees of purity, such as bauxite and bentonite clay; or diatomaceous earth such as kieselguhr. Of the above mentioned oxides, alumina is preferred, and particularly preferred is synthetically prepared substantially anhydrous gamma alumina with a high degree of purity. By a platinum group metal is meant a noble metal, excluding silver and gold, selected from the group consisting of platinum, palladium, germanium, ruthenium, rhodium, osmium and iridium. These metals are not necessarily equivalent in activity in the catalyst and of these metals, platinum and palladium are preferred. Recent findings indicate that in some applications other metals, particularly rhenium and germanium, have a beneficial effect and increase or lengthen catalyst activities. Also normally present in these catalysts is a halogen, termed in the art a combined halogen, and which may be present in an amount of from 0.01 to about 5.0% by weight based on the dried support material, and which is preferably selected from fluorine and chlorine, with chlorine being particularly preferred.

The conditions necessary for successful operation of the reaction zone during isomerization are dependent on both the charge material and the specific catalyst used in the reaction zone. For the specific embodiment of isomerization of $C_5$ and $C_6$ normal paraffins, the inlet temperature to the reaction zone may range from 250° F. to about 400° F. and a more particularly preferred operating range would be from 300° F. to 350° F. The isomerization reaction is exothermic and a temperature rise of 30° F. to 60° F. is normal depending on the degree of conversion and the amount of benzene contained in the charge material. Benzene, which is often present due to poor fractionation of the charge material, exerts a large effect on the reaction zone outlet temperature because the hydrogenation reaction of benzene is more exothermic than the isomerization reaction of the normal paraffin. The reaction zone may be maintained at almost any pressure, but normally the pressure used will be from about 400 psig. to about 1500 psig. with a preferred range being from 800 psig. to 1200 psig. and a particularly preferred operating pressure being about 1000 psig.

The invention may also be applied to processes in which the reaction zone does not contain a catalytic composite. For instance, the invention may be applied to a process for the thermohydrodealkylation of toluene or to the visbreaking process used in petroleum refining. Another application of the invention is the dehydrogenation of normal $C_8$ to $C_{18}$ paraffins as described in U.S. Pat. Nos. 3,391,218; 3,448,165 and 3,647,719. Other processes which may be practiced using the subject invention include, but are not limited to: the disproportionation of aromatic hydrocarbons; the thermocracking of naphthas; the isomerization of naphthenes as, for example, the isomerization of methylcyclopentane to cyclohexane; the reforming of naphthas to produce aromatics or gasoline blending stocks; and the alkylation of paraffinic or aromatic hydrocarbons.

I claim as my invention:

1. A hydrocarbon conversion process which comprises the steps of:
   (a) passing a mixed-phase feed stream into an indirect heat exchange zone and effecting the vaporization of a portion of the feed stream and the heating of the mixed-phase feed stream to a desired temperature;
   (b) passing the mixed-phase feed stream through a reaction zone maintained at mixed-phase hydrocarbon conversion conditions that effect the production of a mixed-phase reaction zone effluent stream and separating a liquid fraction;
   (c) heating at least a portion of the liquid fraction of said mixed-phase reaction zone effluent stream by passage of said portion through a fired heating zone maintained at least 15° F. to 20° F. above the temperature of the reaction zone inlet; and
   (d) cooling at least a portion of said heated reaction zone effluent stream by passage of said effluent stream through the indirect heat exchange zone and indirect heat exchange against the feed stream of step (a).

2. The process of claim 1 further characterized in that all of the heated reaction zone effluent stream is passed to the indirect heat exchange zone.

3. The process of claim 1 further characterized in that the reaction zone contains a bed of isomerization catalyst and is maintained at isomerization conditions.

4. The process of claim 3 further characterized in that the feed stream comprises a $C_7$ to $C_9$ aromatic hydrocarbon which is isomerized within the reaction zone.

5. The process of claim 3 further characterized in that the feed stream comprises hydrogen and a normal paraffin having from 4 to 7 carbon atoms per molecule.

6. The process of claim 1 further characterized in that the reaction zone contains a bed of hydroprocessing catalyst maintained at hydroprocessing conditions and in that the feed stream comprises hydrogen which is partially consumed within the reaction zone.

7. A hydrocarbon conversion process which comprises the steps of:
   (a) passing a mixed-phase feed stream into an indirect heat exchange zone maintained at least 15° F. to 20° F. above the temperature of an inlet of a reaction zone and effecting the vaporization of a portion of the mixed-phase feed stream and the heating of the mixed-phase feed stream to a desired temperature;
   (b) passing said heated mixed-phase feed stream through the reaction zone maintained at hydrocarbon conversion conditions and effecting the production of a mixed-phase reaction zone effluent stream;
   (c) separating the mixed-phase reaction zone effluent stream into a vapor-phase stream and a liquid-phase stream in a vapor liquid separation zone;
   (d) heating the liquid-phase stream in a direct-fired heating zone; and
   (e) cooling at least a portion of said heated liquid-phase stream by passage of said portion through said indirect heat exchange zone of step (a) and indirect heat exchange against said feed stream.

8. The process of claim 7 further characterized in that the entire liquid-phase stream is heated and passed through said heat exchange zone of step (a).

9. The process of claim 8 further characterized in that at least a portion of the vapor-phase stream is recirculated to the reaction zone as part of the feed stream.

10. The process of claim 7 further characterized in that the reaction zone contains a bed of isomerization catalyst and is maintained at isomerization conditions and in that the feed stream comprises hydrogen.

11. The process of claim 7 further characterized in that the reaction zone contains a bed of hydroprocessing catalyst maintained at hydroprocessing conditions and in that the feed stream comprises hydrogen which is partially consumed within the reaction zone.

12. The process of claim 11 further characterized in that hydrogen sulfide is formed within the reaction zone.

13. The process of claim 11 further characterized in that olefinic hydrocarbons are hydrogenated within the reaction zone.

* * * * *